United States Patent
Ramirez et al.

(10) Patent No.: US 7,354,604 B2
(45) Date of Patent: Apr. 8, 2008

(54) HYDROGEN PEROXIDE DISINFECTANT CONTAINING A CYCLIC CARBOXYLIC ACID AND/OR AROMATIC ALCOHOL

(75) Inventors: Jose A. Ramirez, Milwaukee, WI (US); Navid Omidbakhsh, Mississauga (CA)

(73) Assignee: Virox Technologies Inc., Mississauga, Ontario (CA)

(*) Notice: Subject to any disclaimer, the term of this patent is extended or adjusted under 35 U.S.C. 154(b) by 399 days.

(21) Appl. No.: 10/712,990

(22) Filed: Nov. 17, 2003

(65) Prior Publication Data

US 2005/0058719 A1 Mar. 17, 2005

Related U.S. Application Data

(60) Provisional application No. 60/426,306, filed on Nov. 15, 2002.

(51) Int. Cl.
*A61K 33/40* (2006.01)
*A61K 31/31* (2006.01)
*A61K 31/34* (2006.01)
*A61K 31/60* (2006.01)

(52) U.S. Cl. .................. 424/616; 514/159; 514/461; 514/557; 514/572

(58) Field of Classification Search ............. 424/70.13, 424/616; 514/159, 557, 461, 572
See application file for complete search history.

(56) References Cited

U.S. PATENT DOCUMENTS

| | | | |
|---|---|---|---|
| 3,969,258 A | 7/1976 | Carandang et al. | |
| 4,051,058 A | 9/1977 | Bowing et al. | |
| 4,051,059 A | 9/1977 | Bowing et al. | |
| 4,405,482 A | 9/1983 | Hayes et al. | |
| 4,446,153 A | 5/1984 | Yang | |
| 4,477,438 A | 10/1984 | Willcockson et al. | |
| 4,518,585 A | 5/1985 | Greene et al. | |
| 4,525,291 A | 6/1985 | Smith et al. | |
| 4,525,292 A | 6/1985 | Cushman et al. | |
| 4,557,898 A | 12/1985 | Greene et al. | |
| 4,637,899 A | 1/1987 | Kennedy, Jr. | |
| 4,878,951 A | 11/1989 | Pochard et al. | |
| 5,059,417 A | 10/1991 | Williams et al. | |
| 5,149,463 A | 9/1992 | Peterson | |
| 5,171,564 A | 12/1992 | Nathoo et al. | |
| 5,200,189 A | 4/1993 | Oakes et al. | |
| 5,205,960 A | 4/1993 | Kristopeit et al. | |
| 5,244,593 A | 9/1993 | Roselle et al. | |
| 5,264,229 A | 11/1993 | Mannig et al. | |
| 5,387,605 A | 2/1995 | Beilfuss et al. | |
| 5,523,012 A | 6/1996 | Winterton et al. | |
| 5,599,400 A | 2/1997 | Mao et al. | |
| 5,602,090 A | 2/1997 | Melikyan et al. | |
| 5,641,530 A | 6/1997 | Chen | |
| 5,718,910 A | 2/1998 | Oakes et al. | |
| 5,723,400 A | 3/1998 | Morini et al. | |
| 5,723,406 A | 3/1998 | Larose et al. | |
| 5,736,498 A | 4/1998 | Gray | |
| 5,736,582 A | 4/1998 | Devillez | |
| 5,827,542 A | 10/1998 | Miner et al. | |
| 5,855,217 A | 1/1999 | John | |
| 5,891,392 A | 4/1999 | Monticello et al. | |
| 5,900,256 A | 5/1999 | Scoville, Jr. et al. | |
| 6,043,209 A | 3/2000 | Micciche et al. | |
| 6,096,348 A | 8/2000 | Miner et al. | |
| 6,110,883 A | 8/2000 | Petri et al. | |
| 6,296,880 B1 | 10/2001 | Murad | |
| 6,309,470 B1 * | 10/2001 | Schulhoff et al. ............. 134/26 |
| 6,346,279 B1 | 2/2002 | Rochon | |
| 6,383,523 B1 | 5/2002 | Murad | |
| 6,444,636 B1 | 9/2002 | Toussaint et al. | |
| 6,479,454 B1 | 11/2002 | Smith et al. | |
| 6,593,283 B2 | 7/2003 | Hei et al. | |
| 6,617,294 B2 | 9/2003 | Narula et al. | |
| 6,841,090 B1 | 1/2005 | Allighieri et al. | |
| 6,927,237 B2 | 8/2005 | Hei et al. | |

(Continued)

FOREIGN PATENT DOCUMENTS

CA 1 102 502 6/1981

(Continued)

OTHER PUBLICATIONS

MGC Baldry, "The Bactericidal, Fungicidal and Sporicidal Properties of Hydrogen Peroxide and Peractetic Acid", 1982, Journal of Applied Bacteriology 54, pp. 417-423.

Parker et al., "Food Plant Sanitation: Effective Detergency and Cleaning Practice", (New York: Reinhold Publishing Corporation, 1962), pp. 223-263.

"Announcement", (1999), vol. 14, No. 1, The Canadian Journal of Infection Control.

(Continued)

*Primary Examiner*—Sreenivasan Padmanabhan
*Assistant Examiner*—Nathan W. Schlientz
(74) *Attorney, Agent, or Firm*—Clark & Brody (57) ABSTRACT

An aqueous disinfecting solution and dry powdered composition which may be dissolved in water to provide the solution. The solution has a pH of from 0.6 to 7 and comprises (a) hydrogen peroxide in a concentration of from 0.01 to 6% w/w; and (b) at least one component chosen from cyclic carboxylic acids and aromatic alcohols, in a concentration of from 0.01 to 4 w/w %, all based on the total weight of the solution. The cyclic carboxylic acids are preferably 2-furan carboxylic acid, benzoic acid and salicylic acid. Furthermore, the solution preferably contains at least one C6-C12 alkyl diphenyl oxide sulfonate surfactant and a nonionic surfactant. Additional optional ingredients include anionic surfactants, corrosion inhibitors, cation sequestering agents, and buffers.

39 Claims, 2 Drawing Sheets

U.S. PATENT DOCUMENTS

| | | |
|---|---|---|
| 2002/0072288 A1 | 6/2002 | Hei et al. |
| 2002/0168422 A1 | 11/2002 | Hei et al. |
| 2003/0161891 A1 | 8/2003 | Ruiter |
| 2003/0181377 A1 | 9/2003 | Hallahan et al. |
| 2003/0203035 A1 | 10/2003 | Hasan et al. |
| 2003/0206965 A1 | 11/2003 | Hasan et al. |
| 2003/0228996 A1 | 12/2003 | Hei et al. |
| 2004/0033923 A1 | 2/2004 | McClung |
| 2004/0137077 A1 | 7/2004 | Ancira et al. |
| 2004/0171687 A1 | 9/2004 | Kemp et al. |
| 2004/0182793 A1 | 9/2004 | Owens |
| 2005/0019421 A1 | 1/2005 | Hobbs et al. |
| 2005/0058719 A1 | 3/2005 | Ramirez et al. |
| 2005/0133460 A1 | 6/2005 | McClung |
| 2005/0145824 A1 | 7/2005 | McClung |
| 2005/0145825 A1 | 7/2005 | McClung |
| 2005/0145826 A1 | 7/2005 | McClung |
| 2005/0255172 A1 | 11/2005 | Omidbakhsh |
| 2006/0172911 A1 | 8/2006 | McClung |

FOREIGN PATENT DOCUMENTS

| | | |
|---|---|---|
| CA | 1 244 759 | 11/1988 |
| DE | 32 29 097 A1 | 2/1984 |
| DE | 26 29 081 A1 | 6/1987 |
| DE | 35 43 500 A1 | 6/1987 |
| EP | 0057153 | 1/1982 |
| EP | 0087049 | 11/1986 |
| EP | 0 252 278 | 6/1987 |
| EP | 0289463 | 4/1988 |
| EP | 0351772 | 7/1989 |
| EP | 0 456 272 A1 | 5/1991 |
| EP | 0524150 | 7/1992 |
| EP | 0 505 935 A1 | 9/1992 |
| EP | 0 582 359 A1 | 2/1994 |
| EP | 0 582 360 A1 | 2/1994 |
| EP | 0 776 613 A1 | 6/1997 |
| EP | 0845526 | 11/1997 |
| EP | 1 369 037 A1 | 12/2003 |
| EP | 1 374 679 A2 | 1/2004 |
| GB | 1 584 170 | 2/1981 |
| GB | 2101350 | 5/1982 |
| JP | 57-192302 | 8/1982 |
| JP | 10-121097 | 5/1988 |
| JP | 9-87677 | 3/1997 |
| JP | 10-130693 | 5/1998 |
| WO | 98/11777 | 3/1988 |
| WO | WO 98/18894 | 7/1988 |
| WO | 93/04664 | 3/1993 |
| WO | 93/14183 | 7/1993 |
| WO | 95/04001 | 2/1995 |
| WO | WO 97/28691 A1 | 8/1997 |
| WO | 98/18894 | 5/1998 |
| WO | 98/21305 | 5/1998 |
| WO | 98/59028 | 12/1998 |
| WO | 99/02638 | 1/1999 |
| WO | WO 99/03446 | 1/1999 |
| WO | 99/27066 | 6/1999 |
| WO | WO 99/52360 | * 10/1999 |
| WO | 00/27981 | 5/2000 |
| WO | WO 02/055647 A1 | 7/2002 |
| WO | WO03/005817 A2 | 1/2003 |
| WO | WO03/005818 A1 | 1/2003 |
| WO | 03/067989 A1 | 8/2003 |
| WO | 03/076560 A1 | 9/2003 |
| WO | 2004-035718 A2 | 4/2004 |
| WO | WO2004/045281 A2 | 6/2004 |

OTHER PUBLICATIONS

DOWFAX™ Hydrotope Solution.
J.A. Lopes, "Evolution of Dairy and Food Plant Sanitizers Against *Salmonella typhimurium* and *Listeria momocytogenes*", J. Dairy Sci., 69, pp. 2791-2796.
S.A. Sattar, et al., "A Product Based on Accelerated and Stabilized Hydrogen Peroxide, Evidence for Broad-Spectrum Germicidal Activity", Can. J. Infection Control, Winter 1998.
G.R. Dychdala et al., "Surface-Active Agents: Acid-Anionic Compounds", pp. 256-262; XP-002287349.

* cited by examiner

FLOW CHART 1

THE BASIC QUANTITATIVE CARRIER METHOD FOR TESTING THE BACTERICIDAL ACTIVITIES OF LIQUID CHEMICAL GERMICIDES

*The test involved drying a microbial suspension on a hard surface carrier and covering the dried inoculum with the use-dilution of the disinfectant for the specified contact time at room temperature. At the end of the contact time, an eluent/rinse was used to recover the reaction mixture from the carrier and the eluate was passed through a membrane filter (0.22 μm pore diameter) to capture the test organism. The filters were then placed on plates of suitable recovery agar medium and incubated to allow viable organisms to form visible colonies. The numbers of colony forming units (CFU) were recorded and the level of inactivation of the test organism was calculated.*

HYDROGEN PEROXIDE DISINFECTANT CONTAINING A CYCLIC CARBOXYLIC ACID AND/OR AROMATIC ALCOHOL

This application claims priority under 35 USC 119(e) based on U.S. provisional patent application No. 60/426,306, filed Nov. 15, 2002.

FIELD OF THE INVENTION

The present invention relates to acidic aqueous hydrogen peroxide-based disinfecting or sanitizing solutions.

BACKGROUND TO THE INVENTION

In infection control practice, mycobacterial species are typically used as the benchmark for evaluating the potency of a germicide. If a chemical disinfectant is effective in destroying mycobacteria, then it will be judged effective for use as a hard surface disinfectant, against all possible bacterial species and lipophylic and hydrophilic viral particles. For example, in dental practice, a disinfectant registered with the EPA as a tuberculocide is recommended for general hard surface disinfection (CDC, 1993).

Very few liquid chemical disinfectants are effective sporicides, particularly in cold soaking instruments sensitive to chemical attack. The most widely used sporicidal chemical solutions are based on aldehydes, short chain alcohols, phenolic compounds, and certain peroxygens. Aldehydes (e.g. formaldehyde and glutaraldehyde), although highly effective, suffer from serious occupational safety and environmental disposal hazards. Of the peroxygens, peracids are those most widely used in liquid form. Peracetic and performic acids have been marketed for the disinfection of semicritical and critical instruments; however, their aggressive chemical nature tend to damage surfaces and instruments with prolonged use.

Alcohol or phenolic compounds which exhibit good efficacy against mycobacterial species are typically not effective in destroying bacterial endospores. Mycobactericidal products that are based on short-chain alcohols typically contain these ingredients at high concentrations (usually higher than 20% w/w). This makes the products highly flammable and toxic. Furthermore, they are often characterized by a strong alcoholic odor and are therefore difficult to use in large quantities in small enclosed spaces by chemically sensitive individuals. Phenolic compounds can be used by themselves or in combination with other germicidal actives (such as with quaternary ammonium compounds and solvents), in order to achieve wide spectrum efficacy. These compounds are also highly volatile and exhibit strong objectionable odors.

Hypochlorite solutions and other chlorine-based compounds are effective against both mycobacteria and bacterial endospores; however, they are easily inactivated by the presence of organic matter, are unstable when diluted, have a strong, objectionable, chlorinated smell, and are highly corrosive and therefore damaging to most instruments and surfaces.

Aqueous chemical disinfectants are used in applications where, due to occupational, environmental, or toxicological concerns, solvent-based solutions cannot be used. While there are a large number of disinfecting and sanitizing solutions available in the marketplace, there is still a need for a low-volatility, low toxicity, non-corrosive, non-irritating, and stable aqueous disinfectant which is effective against hydrophilic viruses, acid-fast bacteria and bacterial endospores. The present invention is intended to at least partially address this need.

SUMMARY OF THE INVENTION

The present invention provides, in accordance with a first aspect, aqueous, acidic, hydrogen peroxide based solutions, embodiments of which can be, surprisingly, highly effective against mycobacteria and bacterial endospores. Solutions according to the present invention have a pH of from 0.6 to 7 or from 0.6 to 5. Some embodiments of the present inventive solution may have a pH of from 1.9 to 2.1, while other embodiments may have a pH of from 2 to 4 or from 4 to 5. The present inventive solutions comprise (a) hydrogen peroxide in a concentration of from 0.01 to 6, or from 0.25 to 4% w/w; and (b) at least one component chosen from cyclic carboxylic acids and aromatic alcohols in a concentration of from 0.01 to 4% w/w, all based on the total weight of the solution. The at least one component may be present in a concentration of from 0.1 to 2.5% w/w, or from 0.25 to 1.0% w/w, or 0.4 to 0.6% w/w, based on the total weight of the solution. The cyclic carboxylic acid is preferably 2-furan carboxylic acid (also referred to herein as 2-furoic acid), benzoic acid and salicylic acid. The aromatic alcohol is preferably benzyl alcohol.

To achieve the desired pH values, the solution may contain acid or alkaline buffers such as phosphoric acid, citric acid, glycolic acid, lactic acid, sodium carbonate, calcium carbonate, sodium carbonate, potassium hydroxide, sodium hydroxide, and ethanolamine.

In one embodiment, the solution may further comprise at least one nonionic surfactant in a concentration of from 0.005 to 3% w/w, preferably from 0.01 to 3% w/w, more preferably from 0.01 to 1% w/w, and even more preferably from 0.04 to 0.06% w/w, based on the total weight of the solution. Furthermore, the at least one nonionic surfactant is preferably chosen from (a) ethoxylated alcohols and alkylglycosides having a hydrophile lyophile balance from 5 to 15, which may be a C6-C10 alkyl, 3.5 moles of ethylene oxide (EO) alcohol ethoxylate; and (b) a sufficiently water-soluble block copolymer of ethylene oxide or propylene oxide.

In yet another embodiment, the solution may further comprise at least one cation sequestering agent in a concentration of from 0.01 to 6% w/w, preferably from 0.05 to 2% w/w, more preferably from 0.1 to 2% w/w, and even more preferably from 0.5 to 1% w/w, based on the total weight of the solution. The cation sequestering agent may be 1-hydroxyethylidene-1,1-diphosphonic acid.

In still another embodiment of the invention, the solution may contain at least one anionic surfactant chosen from (a) C8-C16 alkyl benzene sulfonic acids and alkali metal, alkaline earth metal, ammonium or alkylamine salts thereof; (b) C8-C18 alkyl sulfonic acid; (c) C8-C16 alkyl sulfates; and (d) C6-C12 alkyl diphenyl oxide sulfonate surfactants, in a concentration of from 0.01 to 10% w/w, or from 0.01 to 6% w/w, 0.01 to 5% w/w, 0.01 to 3% w/w, or 0.05 to 1% w/w, based on the total weight of the solution. The at least one anionic surfactant may be an alkyl benzene sulfonic acid and, preferably, dodecyl benzene sulfonic acid.

In an embodiment suitable for inactivating resistant, hydrophilic viruses, the solution may further comprise a C6-C12 alkyl diphenyl oxide sulfonate surfactant in a concentration of from 0.01 to 5% w/w, 0.05 to 3% w/w, 0.05 to 2% w/w, or from 0.05 to 1.5% w/w, based on the total weight of the solution. The surfactant may be a C10 alkylated sulfonated diphenyl oxide sodium salt.

Solutions according to the present invention may comprise at least one corrosion inhibitor in a concentration of from 0.001 to 15% w/w, 0.001 to 5% w/w, 0.01 to 1% w/w, 0.01 to 0.5% w/w, or 0.02 to 0.22% w/w, based on the total weight of the solution. The at least one corrosion inhibitor may be chosen from 1,2,3 benzotriazole, sodium molybdate, sodium nitrite, sodium bisulfate, sodium metabisulfate, chromates, borates, phosphates, polyphosphates, sodium benzoate, sodium silicate and sodium gluconate.

The solution may further contain a hydrotrope in a concentration of from 0.01 to 15% w/w, based on the total weight of the solution, which may be sodium xylene sulfonate. Furthermore, the solution may include from 0.1 to 20% w/w of a solvent such as a glycol or glycol ether (e.g. propylene glycol).

The water used in solutions according to the invention may be tap water, deionized water, or a mixture thereof.

The invention provides, in accordance with a second aspect, a concentrated aqueous, acidic disinfecting solution which may be diluted with water to provide a solution according to the first aspect of the invention. Such solution may have a total cyclic carboxylic acid and aromatic alcohol concentration of up to 30% w/w, based on the total weight of the solution.

The invention provides, in accordance with a third aspect, a dry particulate composition dissolvable in water to produce an aqueous disinfecting solution according to the first or second aspects of the invention. In such embodiments, the composition comprises at least one hydrogen peroxide releasing component, which may be chosen from sodium percarbonate, sodium perborate monohydrate, and sodium perborate tetrahydrate.

In accordance with a fourth aspect, the invention provides a two or multi-component system, each component of which may be in either liquid or dry form which, when combined, will provide a disinfecting solution or composition according to any one of the first, second and third aspects.

DETAILED DESCRIPTION OF PREFERRED EMBODIMENTS

The present invention is intended to provide a rapid-acting hydrogen peroxide-based liquid disinfectant containing low levels of active ingredients. Some embodiments are suitable for high level disinfection. In this context, "high level disinfection" means the destruction of mycobacterium species as well as bacterial endospores to the degree required in semicritical and critical applications, as measured by standard carrier testing methods.

Solutions according to the present invention are effective germicides, are low in toxicity and employ biodegradable ingredients. The result is a disinfectant which does not suffer from the occupational safety or environmental disposal problems associated with current technologies. Because of the low levels of hydrogen peroxide and other supplemental ingredients, "in use" solutions according to the present invention exhibit very low reactivity towards material substrates and tissue, and are therefore non-corrosive to skin or metals. The low hydrogen peroxide concentrations also result in improved shelf life and ease of packaging, as vented packaging would not be required.

The present invention provides solutions which are a dramatic improvement over existing hydrogen peroxide disinfectants. Contact times in high level disinfection may be reduced by factors of up to 4-5, using hydrogen peroxide concentrations which are lower by as much as one order of magnitude compared to prior art solutions.

The present solution may be used in the disinfection of semicritical and critical surfaces and/or instruments, as well as noncritical surfaces where use of an anti-tuberculosis disinfectant is recommended. Such a disinfectant is common in the dental industry and in health care settings for disinfecting respiratory equipment. A major field of application is in the processing of delicate surgical instruments and devices, including flexible endoscopes. The rather mild, non-reactive nature of the components in the mixture, and the low levels at which they are formulated, make the solution ideal for the processing of flexible medical devices, while at the same time ensuring complete disinfection, even in the presence of organic matter.

Without being bound by theory, it is believed that the hydrogen peroxide in solutions of the present invention is central to the mechanism of disinfection. Hydrogen peroxide is believed to disrupt functions vital to the microorganism cell, for example, by inhibiting the assembly of ribosomes units within the cytoplasm of the cell. Furthermore, the decomposition of hydrogen peroxide in the solution results in the generation of hydroxyl free radicals which are believed to attack proteins and nucleic acids.

The hydrogen peroxide used in the present solution is typically a commercially available aqueous solution, usually in a concentration of 10-50% w/w. Commercial solutions for hydrogen peroxide may contain additional stabilizers and additives as are known in the art. In the present inventive solution, the preferable concentrations of hydrogen peroxide ranges from about 0.01 to about 6% w/w and more preferably from about 0.25 to about 4% w/w. While solutions with higher concentrations of hydrogen peroxide can be advantageously used, they are typically highly corrosive and have material compatibility problems. Thus, they cannot be applied in practice for the disinfection of delicate instruments. They can also be hazardous and associated with occupational safety and shipping restrictions.

It is recognized that the above specified low levels of hydrogen peroxide can be achieved by dilution of a more concentrated stock solution. Moreover, a dry particulate composition may be formulated for mixing with water by an end user to produce a solution according to the present invention. Hydrogen peroxide is commercially available in a dry form as persalt compounds, of which the preferred ones are sodium percarbonate and sodium perborate in its monohydrate and tetrahydrate forms. Since sodium percarbonate contains about 20% equivalent hydrogen peroxide by weight, and sodium perborate monohydrate and tetrahydrate contain about 30% and 20% respectively by weight, proper allowance must be made when blending the dry mixture of components to achieve the desired levels of hydrogen peroxide upon dissolution in water.

Solutions according to the present invention also contain at least one component chosen preferably from 2-furan carboxylic acid, benzoic acid, salicylic acid and benzyl alcohol, in a concentration of from 0.01 to 8% w/w or from 0.01 to 4% w/w of the total solution. Furan carboxylic acids are naturally occurring degradation products of lignin and cellulose. 2-furan carboxylic acid has been described as possessing some bactericidal, fungicidal and mycobactericidal activity, particularly when formulated in combination with traditional mycobactericidal ingredients. The 2-furan carboxylic acid employed in the present invention is available commercially in crystalline form, as it is typically manufactured in bulk through the Cannizaro reaction of furfural at highly alkaline conditions. It is recognized that 2-furan carboxylic acid from other sources can also be employed. For example, it may be obtained through the microbial decomposition of cellulose.

Benzyl alcohol occurs naturally in essential oils of vegetable origin. Commercially, benzyl alcohol is commonly manufactured from the reaction of benzyl chloride and sodium carbonate. Benzyl alcohol is used as a photographic developer for color movie film and in perfumes, flavour industries, pharmaceuticals as a bacteriostatic, cosmetics, ointments, emulsions, textiles, sheet plastics and inks. Benzyl alcohol has a vapor pressure lower than 0.1 mmHg (at 20 degrees C.) which meets the standards of CARB California Air Resources Board for volatile organic compounds.

If inactivation of hydrophilic viruses is desired, the solution may contain at least one C6-C12 alkyl diphenyl oxide sulfonate surfactant (e.g. alkyl diphenyl oxide disulfonate surfactant). This ingredient has been found to not only impart hydrotroping and detersive properties to the mixture, but also, surprisingly, to play a key role in the inactivation of difficult to mitigate hydrophilic viruses. The inclusion of this ingredient is believed to provide the necessary broad activity spectrum of a tuberculocidal product. Examples of this ingredient are the alkyl diphenyl oxide disulfonate surfactants manufactured commercially by the Dow Company in association with the trademark DowFax. The preferred concentration of this ingredient is from 0.05 to 3.0% w/w of the solution.

The solution may also contain from 0.005 to 3.0% w/w of at least one nonionic surfactant chosen from the family of ethoxylated alcohols and alkylglycosides of hydrophile lyophile balance between 5.0-15.0, or from the group of sufficiently water-soluble block copolymers of ethylene oxide or propylene oxide. These ingredients impart low surface tension to the solution, improving its wetting and detergency properties. These surfactants are stable in the presence of acid hydrogen peroxide media, and do not contribute to excessive hydrogen peroxide decomposition. They are available commercially from numerous manufacturers. Examples include surfactants sold in association with (a) the trademark Alfonic by Condea Vista, (b) the trademark Tergitol by Union Carbide, and (c) the trademark Pluronic and Tetronic by BASF. The solution may also contain at least one anionic surfactant chosen from C8-C16 alkyl benzene sulfonic acids and alkali metal, alkaline earth metal, ammonium or alkylamine salts thereof, C8-C18 alkyl sulfonic acid, or C8-C16 alkyl ethoxylated or non ethoxylated sulfates, in a concentration of from 0.01 to 5.0% w/w of the mixture. These ingredients help impart detersive properties to the solution, and are particularly useful if the solution is used in a cleaning step prior to formal disinfection. These ingredients are available commercially from many vendors. Examples include products sold in association with the trademarks Biosoft and Stepanol by Stepan and the trademark Hostapur by Hoechst.

Chelating agents may be included in the solution of the invention to enhance cleaning performance and stability of the solution. Examples include 1-hydroxyethylidene-1,1-diphosphonic acid sold commercially by Solutia in association with the trademark Dequest 2010, and aminotrimethylene phosphonic acid sold commercially by Allbright and Wilson in association with the trademark Dequest 2010. Polycarboxylate chelators may be employed. Examples include ethylenediaminetettraacetic acid, hydroxyethyl-ethylenediaminetriacetic acid, 2-hydroxyethyl-iminodiacetate (HEIDA) and nitrilotriacetic acid. Chelating agents aid the detergency process by sequestering cationic species responsible for the inactivation of anionic surfactants by cation-anion coupling, by increasing the zeta potential between substrates and soil particles, and by dissolving larger soil aggregates held together by cation bridging.

Other ingredients which are sufficiently stable in the presence of hydrogen peroxide, and at the acid conditions of the present solution may be added to impart desirable qualities. Suitable dyes and fragrances may be employed for modifying the color and odor of the solution. Thickening agents may be added to modify its Theological properties. Corrosion inhibitors may also be added provided they are compatible with hydrogen peroxide in an acid medium and do not adversely affect the germicidal properties of the solution. Such ingredients include, but are not limited to, benzotriazoles, tolutriazoles, sodium nitrite, and sodium molybdate.

Solutions of the present invention can be readily prepared by serial addition of the above-mentioned ingredients to deionized water. For optimum product stability, the water should have an electrical conductivity of less than 200 μS. Water purified by ion exchange or reverse osmosis is suitable for this purpose. The first ingredient(s) to be added to the required amount of water is the at least one component chosen from 2-furan carboxylic acid, benzoic acid, salicylic acid and benzyl alcohol. These ingredients are not highly soluble and therefore require more time to dissolve than the other ingredients. About 95% of the final water content of the solution is added to a mixing vessel made of high density polypropylene or passivated austenitic stainless steel, and equipped with a stirrer with shaft and blades constructed of these same materials. After addition of the at least one component and allowing sufficient time for its complete dissolution (e.g. between 0.5 to 1 hr), the rest of the ingredients can be added serially in no particular order, allowing between 30 to 45 minutes of stirring between each addition. It is preferred that the hydrogen peroxide be added as the final ingredient.

As mentioned previously, a preferred embodiment of the invention may be in dry form. In this case, one would add, in a tumbling or ribbon mixer for powdered solids, the appropriate amounts of the crystalline form of each ingredient and, optionally, a suitable crystalline filling substance such as sodium sulfate. Commercially available persalt compounds would be employed in lieu of aqueous hydrogen peroxide. Preferred examples include sodium percarbonate and sodium perborate in its monohydrate and tetrahydrate forms.

Alternatively, one can formulate a dry mixture containing all ingredients except the benzyl alcohol and hydrogen peroxide or dry hydrogen peroxide releasing components. This mixture would then be added to the benzyl alcohol and hydrogen peroxide in aqueous or dry form at the moment of use. This application is useful when using automatic machines that are equipped for dosing and mixing two-part systems.

As mentioned above, the present solutions are suitable for the disinfection of delicate and chemically sensitive materials with minimal occupational safety risks. Some embodiments of the present invention are particularly useful in the disinfection of semi-critical and critical surfaces and instru- ments in the health care, veterinary care and dental care industries. Specific applications include, but are not limited to, the cleaning and disinfection of invasive and non-invasive surgical equipment, the cleaning and disinfection of rigid and flexible invasive and non-invasive diagnostic equipment, the cleaning and disinfection of prostheses and implants, the internal cleaning and disinfection of body fluids recirculating machinery, and the cleaning and disinfection of non-critical surfaces where the use of products with tuberculocidal efficacy is recommended, such as dental chairs and respiratory resuscitation equipment.

The methods of application of the present disinfecting solution include, but are not limited to, spraying the solution on the surface to be treated with a spraying trigger or nozzle, simply wetting the area or instrument with the solution, filling an enclosed space (a tube for example) with the solution and allowing the solution to sit there for the required contact time, and circulating the solution through internal conduits and passages of an instrument for a predetermined period of time. The solution can be applied at room temperature or at another temperature (i.e. from 4° C. to as high as 70° C.).

When the present invention is prepared as a dry mixture, the above mentioned application methods can still be used; however, the dry mixture must first be dissolved in water to produce the present aqueous solution. Preparation of the present aqueous solution may be done in-situ or just prior to use, either manually or automatically in a washing disinfection machine equipped for handling powders.

The following examples are intended simply to illustrate the preferred embodiments of solutions according to the present invention and should not be regarded as narrowing in scope. One skilled in the art will readily recognize that these examples suggest many other ways in which the present invention could be practised.

Compounds recited herein have the following chemical formulas:

Benzoic acid

Salicylic acid

Benzyl alcohol 2-furan carboxylic acid 1-hydroxyethylidene-1,1-diphosphonic acid Dodecyl benzene sulfonic acid Phosphoric acid -continued 1,2,3 benzotriazole Sodium xylene sulfonate Glycol Compositions I and II were prepared by the general method described above and the ingredients and their amounts are listed in the tables below.

Composition I

| Ingredient | % w/w whole basis | % w/w active basis (active concentration in solution) |
| --- | --- | --- |
| hydrogen peroxide (50%) | 1.00 | 0.50 |
| 2-furan carboxylic acid (97%) | 0.50 | 0.48 |
| Dowfax C10L (45%) | 0.18 | 0.08 |
| Alfonic L610-3.5 (100%) | 0.05 | 0.05 |
| phosphoric acid (75%) | 2.00 | 1.50 |
| Biosoft S-100 (98%) | 0.18 | 0.176 |
| Briquest ADPA 60-AW (60%) | 0.50 | 0.30 |
| deionized water | 94.59 | 96.908 |
| pH | 1.8 | 1.8 |

This solution is particularly useful as a hard surface cleaner. DowFax C10L is a 45% active, C10 alkylated sulfonated diphenyl oxide disodium salt dissolved in water and manufactured by The Dow Chemical Company. Alfonic L610-3.5 is a 100% active C6-C10 alkyl, 3.5 moles of ethylene oxide (EO) alcohol ethoxylate (AE). This is an alcohol-based nonionic surfactant, ethoxylated to an average of 3.5 moles of ethylene oxide per mole of alcohol, manufactured by Condea Vista. Biosoft S-100 is a 98% active dodecyl benzene sulfonic acid manufactured by Stepan. Briquest ADPA 60 AW is a 60% active 1-hydroxyethylidene-1,1-diphosphonic acid sold by Allbright and Wilson. Phosphoric acid was added for buffering the solution pH to the desired 1.8, while 1-hydroxyethylidene-1,1-diphosphonic acid was added for prolongation of the hydrogen peroxide stability.

Composition II

| Ingredient | % w/w whole basis | % w/w active basis (active concentration in solution) |
| --- | --- | --- |
| hydrogen peroxide (50%) | 1.50 | 0.75 |
| 2-furan carboxylic acid (99%) | 0.38 | 0.376 |
| Cobratec 99 (99%) | 0.12 | 0.119 |
| sodium molybdate (100%) | 0.015 | 0.015 |
| sodium nitrite (100%) | 0.015 | 0.015 |
| sodium carbonate (100%) | 0.09 | 0.09 |
| tap water | 96.90 | 98.635 |
| pH | 4.0 | 4.0 |

All components of Composition II, with the exception of the hydrogen peroxide, were mixed as dry powders to form a dry powdered mixture. Then, prior to use, this powdered mixture and the required amount of aqueous hydrogen peroxide were added to the appropriate amount of tap water. Composition II contains optional ingredients namely, Cobratec 99, sodium molybdate, and sodium nitrite to help mitigate corrosion in metal substrates. Cobratec 99 is a 99% active dehydrated 1,2,3 benzotriazole, manufactured by PMC Specialties Group. Sodium carbonate is an alkaline buffer for buffering the solution to the desired pH of 4.0.

EXAMPLE I

Composition I was tested for bactericidal, virucidal, fungicidal and mycobactericidal activity using a quantitative carrier test method. Its effectiveness as a sanitizer was tested using a suspension test method. These methods will be described further below.

Materials and Methods

Carriers

The inside bottom surface of glass vials (Galaxy Co., Newfield, N.J.) was used as the carrier for all tests except those against the virus.

Soil Load

For inoculation of the carriers, all test organisms were first suspended in bovine serum (Gibco BRL Life Technologies Cat. No. 16000-044, NY, USA), at a final concentration of 5% w/w.

Neutralizer, Microbial Diluent and Filter Rinse

Letheen Broth (with 0.1% w/w sodium thiosulfate pentahydrate) was used as the neutralizer and to rinse the membrane filters and the filter holder unit. A 1% w/w sodium thiosulfate pentahydrate in LB was used as neutralizer for testing with *Pseudomonas aeruginosa*. Normal saline was used to make dilutions of the bacterial suspensions and as the final rinse of the carrier vials and the filter holder unit to aid in rinsing off the froth created by the Letheen broth.

Test Organisms

Standard strains of *Pseudomonas aeruginosa* (ATCC 15442), *Staphylococcus aureus* (ATCC 6538), *Salmonella choleraesuis* (ATCC 10708), *Mycobacterium terrae* (ATCC 15755), *Trichophyton mentagrophytes* (ATCC 9533) and the Sabin vaccine Strain of poliovirus type 1 (ATCC VR-192) were used. A seed culture of *Acinetobacter baumannii* was also used. Vancomycin Resistant *Enterococcus* (VRE) and Methicillin Resistant *Staphylococcus aureus* (MRSA) were cultured as follows:

a) *Staphylococcus aureus* (ATCC 6538), *Salmonella choleraesuis* (ATCC 10708): *Acinetobacter baumanni*, MRSA and VRE: Stock suspensions of five of the six vegetative bacteria were prepared by culturing them in tryptic soy broth (TSB) for 24 hours at 37° C. *Pseudomonas aeruginosa* (ATCC 15442) was grown in 1:1000 TSB for 72 hours at 37° C.

b) *Mycobacterium terrae* (ATCC 15755): The mycobacterium was grown in Middlebrook 7H9 broth with ADC enrichment and glycerol, in vented plug seal capped tissue culture flasks. The test suspension was prepared from stocks grown for 21 days. The cell suspension was washed 3 times by centrifugation at 2,500 rpm for 15 minutes and re-suspended in sterile distilled water. The final stock suspension was prepared by re-suspending the bacterial pellets in sterile bijoux bottles containing glass beads to approximately $10^8$ cells/mL. The stock suspension was stored at 4° C.

c) *Trichophyton mentagrophytes* (ATCC 9533): A stock suspension of the conidia was obtained by inoculating the center of a Mycobiotic Agar plate and incubating it at 28° C. for 10 days. Mycelial mats were harvested from the agar surface, homogenized with sterile glass beads in normal saline and filtered through sterile cotton gauze to remove the hyphae.

d) The Sabin vaccine strain of poliovirus type 1 (ATCC VR-192): A stock of the virus was prepared by infecting monolayer of Vero cells in 75 cm² flasks. The virus was allowed to adsorb to cells for 60 minutes at 37° C. and the infected monolayer kept in minimal essential medium, without any antibiotics and serum, until approximately 75% of the monolayer has been affected by the virus cytopathic effect. The culture was then frozen (−20° C.) and thawed three times and the suspension was centrifuged at 1,000-× g for 10 minutes to remove cellular debris. The supernatant was used as the virus pool.

The Test Methodology

Quantitative Carrier Test (QCT)

Figure 1:
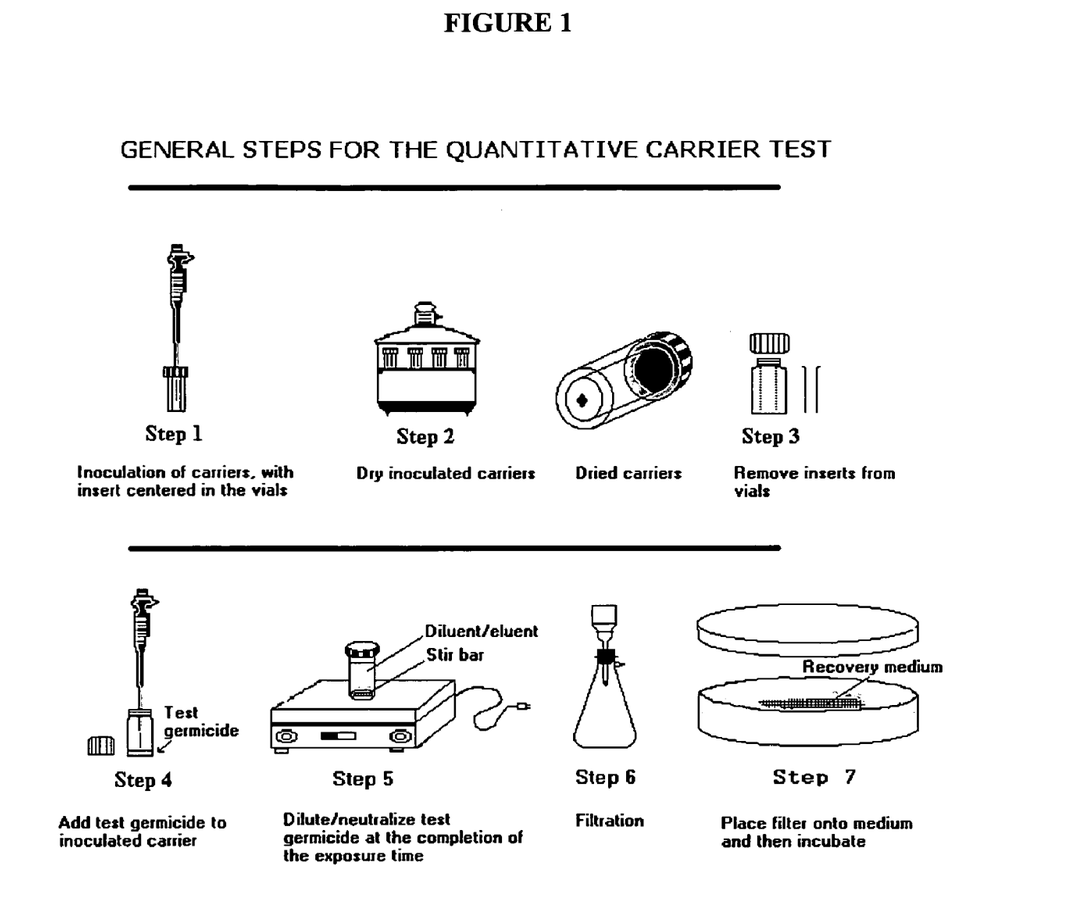
FIG. 1 illustrates the general steps for the Quantitative Carrier Test method used in experiments described herein.
Figure 2:
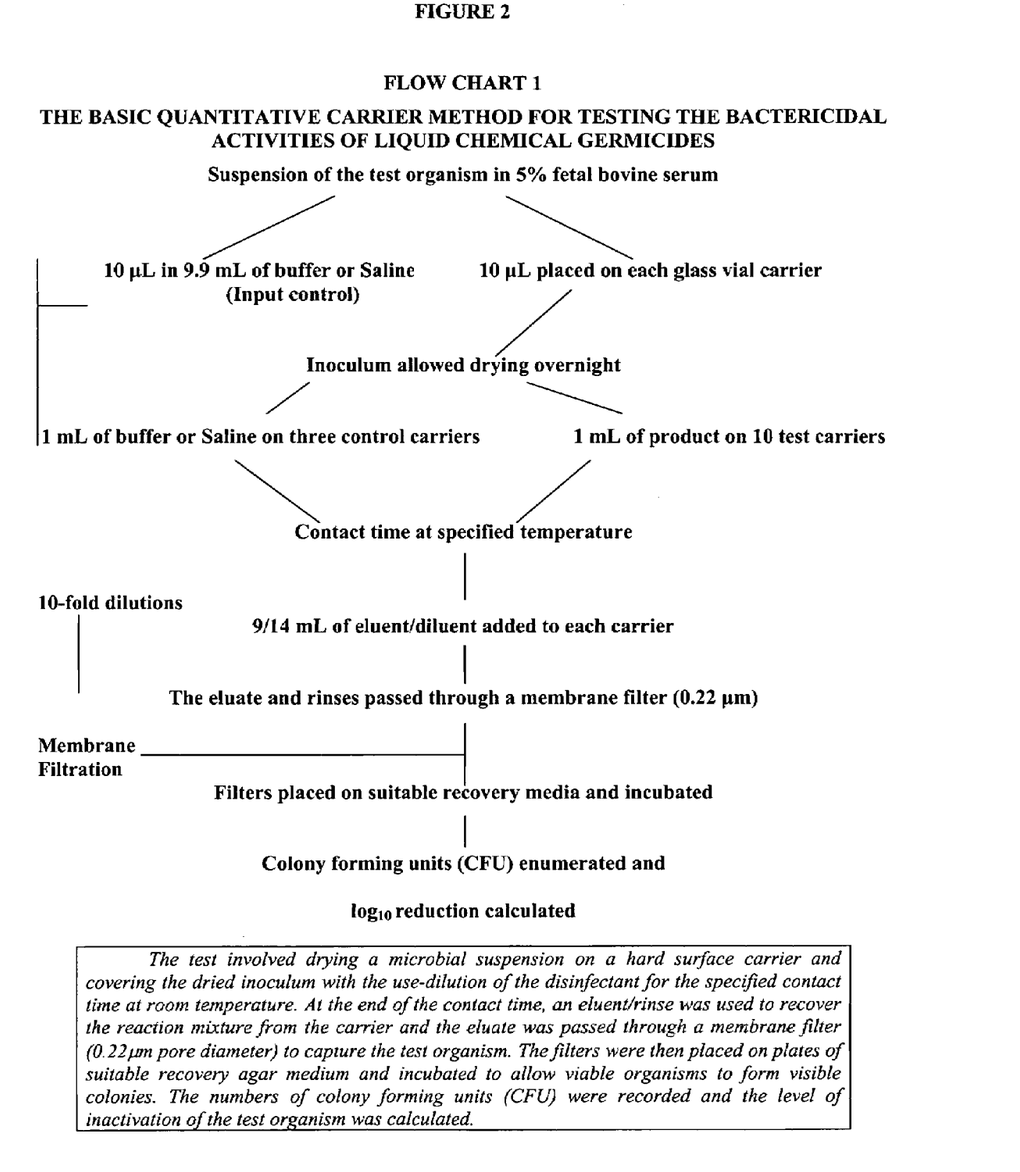
FIG. 2 is a flowchart illustrating the steps of the Quantitative Carrier Test method for testing the bactericidal activities of liquid chemical germicides.

The quantitative carrier tests used in the tests were designed to: (a) permit the determination of the exact number of colony forming units (CFU) or plaque forming units (PFU) placed on each carrier and the CFU/PFU remaining after the drying of the inoculum, (b) avoid wash-off of any of the test organism, (c) allow complete recovery of the inoculum from the carrier surface, (d) arrest the test product's activity by dilution immediately at the end of the contact time, (e) in the case bactericidal tests, capture all the bacterial cells of the test organism on a membrane filter before and after exposure to the test product, (f) removal of any residual germicidal activity by a thorough rinsing of the membrane filter, (g) allow a ratio of 1:100 between the volume of the test microbial inoculum and the volume of the product being evaluated, (h) incorporate glass inserts to eliminate any false-positive results due to the generation of micro-aerosols in the carriers and (i) give a precise determination of $\log_{10}$ reduction in CFU/PFU of the test organism after exposure to the product under test. This test method which is illustrated in FIGS. 1 and 2 eliminates the deficiencies associated with the AOAC Use-Dilution Test (AOAC, 1990) while meeting the Canadian General Standards Board's requirements for germicide test methodology (CGSB, 1997). As stated above, it is now an accepted standard of ASTM (E2111).

The Suspension Test

The test was carried out by adding 100 μL of the bacterial suspension with soil load to 900 μL of the test product in a 2 mL capacity cryovial, vortexed to mix and allowed to sit for the required contact time at room temperature. At the end of the contact time, the reaction mixture received 14.0 mL of the neutralizer and vortexed. This mixture was passed through a membrane filter and the vial was rinsed 2× with 10.0 mL of saline. The membrane filtration technique was the same as that in the quantitative carrier test for bactericidal activity.

Recovery Media and Detection of Viable Organisms

For bactericidal testing using *S. aureus, P. aeruginosa, choleraesuis, A. baumannii*, VRE and MRSA the filters were placed on TSA plates, incubated at 37° C., monitored, and the CFU recorded at 24 hour intervals for a total of 5 days. For mycobactericidal testing using *M. terrae*, the filters were placed on 7H11 agar, incubated at 37° C., monitored, and the CFU recorded at weekly intervals for a total of 4 weeks. For fungicidal testing with *T. mentagrophytes*, the filters were placed on Sabouraud's dextrose agar and incubated at 28° C., monitored, and the CFU recorded at 4 days, and every 24 hour interval thereafter for a total of 10 days Controls For the quantitative carrier test for bactericidal activity, control carriers were used in the same manner as test carriers except that normal saline was applied to the dried inoculum instead of the test product.

Suspension Test—Controls were tested by adding 100 µL of bacterial suspension to 900 µL Letheen broth instead of the disinfectant.

Virucide Test

Stainless steel disks (1 cm in diameter) were used as carriers and each disk placed in each well of a 12-well cell culture plate. Each carrier received 10 µL of the test virus containing 5% serum as soil load. After the inoculum had been allowed to dry, each disk in each well was either exposed to 50 µL the test product or EBSS for the required contact time at room temperature. At the end of the contact time, 950 µL of EBSS was added to both the test and control wells as eluent/neutralizer. A pipette was used to suck the eluent in and out onto the carriers to remove inoculum off the carriers. The eluate was transferred into a sterile labeled dilution vial, vortexed to mix. The control and test eluates were serially diluted and inoculated into cell culture monolayer for virus plaque assays. The plaque forming units (PFU) were determined and $\log_{10}$ reduction calculated.

Plaque Assay For Poliovirus

Confluent monolayers of Vero cells were trypsinized and dispensed into 12-well cell culture plates (Corning cat #08-757-16B) for all plaque assays. The cells were dispensed at a density (approximately $1\times10^6$ cells/well) to allow for formation of confluent monolayers within 24-48 hours. Each assay included three wells as cell controls and each dilution of the sample tested was inoculated into at least three wells.

The growth medium from each plate was aspirated and 100 µL of the appropriate dilution of the test virus suspension was then dispensed directly onto each monolayer. Each dilution was titrated in triplicate. The plates were incubated for 60 minutes at 37° C. in a 5% $CO_2$ atmosphere to allow for virus adsorption. Each monolayer was overlaid with 2 mL of an overlay medium containing 2× MEM supplemented with HEPES, L-glutamine, non-essential amino acids (NEAA), and 2% FBS, 26 mM $MgCl_2$ and Noble Difco Agar. The ratio of the agar and the supplemented medium was 1:1. Once the overlay had solidified, the plates were held for 40 hrs in a 5% $CO_2$ atmosphere at 37° C.

At the end of the required incubation period for the plaque assay, 2 mL of a 3.7% solution of formaldehyde in saline was added to each well and the plates were left for three to four hours to fix the cells and inactivate the virus. The fixative and the agar overlay were then removed from each plate and each well received 2 mL of a 0.1% aqueous solution of crystal violet to stain the cells. Following a contact time of about five minutes, the stain was aspirated, the well washed in tap water and the plates allowed to dry to determine the plaque counts.

Neutralization Verification

Bactericidal Test

One part of the use-dilution of the product was mixed with 14 parts of the neutralizer. The test organism was added to the neutralized solution to give an estimated 20-100 CFU. The neutralizer alone was used as the control solution. At the end of a contact time of 5 minutes at 20° C., the mixture was passed through a membrane filter to capture the bacteria. The filters were placed on the appropriate recovery medium. The plates were incubated and the colonies counted.

The time of 5 minutes was selected in these experiments because it was the maximum delay that could between the initial dilution of the product in the carrier vial and the last lot of rinse passed through the membrane filter.

Virucidal Test

To determine if the dilution of the product at the end of the contact time was sufficient to render it ineffective against the test virus, 100 µL of the test virus was added to 900 µL of a 1/100 dilution of the test product. The same amount of virus was also added to 900 µL of EBSS to act as a control. The tubes were allowed to stand for 5 minutes and they were then inoculated onto cell monolayer for virus plaque formation.

Toxicity and Interference with Plaque Formation:

To determine the effect of the diluted test product on the cell monolayer and the plaque forming ability of the test virus, 100 µL of a 1/100 dilution of the test product was placed into six wells of a twelve-well plate while the other six wells received EBSS as control and allowed to incubate for 30 minutes. The cells were observed under the microscope for signs of toxicity of the test product. The cells were then washed once with EBSS and virus diluted to give countable plaques/well was added to each well. The virus was allowed to adsorb for 60-90 minutes at 37° C. Each cell monolayer was then overlaid and the plates incubated at the appropriate temperature for the development of the virus plaques.

Product Performance Criteria

The numbers of test carriers in the bactericidal and virucidal test were between 5-10. Each test also included three control carriers. The results were reported as $\log_{10}$ reductions in viability in reference to the control carriers.

For a product to be considered an effective disinfectant it was expected to reduce the viability titre of each bacterial test organism by at least 6 $\log_{10}$ (at least 1 million-fold), the fungus by $\geq 5$ $\log_{10}$ and the virus by $\geq 3$ $\log_{10}$ under the conditions of this test. In sanitizer tests, the target was a minimum reduction of 5 $\log_{10}$. If the product is for use in destroying mycobacteria on non-critical surfaces in intermediate level disinfection, the criterion is a minimum 4 $\log_{10}$ reduction (Therapeutics Products Programme; 1999 Ed.; Disinfectant Drug Guidelines; Appendix II; Health Canada, Ottawa, Ontario).

RESULTS

Table 1 below summarizes the results of tests against *Staphylococcus aureus*. All three trials were able to bring about a >7$\log_{10}$ reduction in the viability titre of *S. aureus* in a contact time of 5 minutes at room temperature indicating bactericidal activity against this organism.

TABLE 1

The activity of Composition I against *Staphylococcus aureus*

| Trial | Contact Time (minutes) | CFU/Control Carrier | Average CFU Test Carrier | $\log_{10}$ Reduction |
|---|---|---|---|---|
| 1 | 5 | $1.11 \times 10^7$ | 0 | 7.74 |
| 2 | 5 | $1.11 \times 10^7$ | 0 | 7.74 |
| 3 | 5 | $1.11 \times 10^7$ | 0 | 7.74 |

Table 2 below summarizes the results of the suspension test. All three trials were able to bring about a 6$\log_{10}$ reduction in the viability titre of *S. aureus* in a contact time of 30 seconds at room temperature indicating bactericidal activity against this organism.

TABLE 2

The activity of Composition I against *Staphylococcus aureus*

| Trial | Contact Time (seconds) | CFU/Control Carrier | Average CFU Test Carrier | $Log_{10}$ Reduction |
|---|---|---|---|---|
| 1 | 30 | $9.50 \times 10^5$ | 0 | 5.97 |
| 2 | 30 | $9.50 \times 10^5$ | 0 | 5.97 |
| 3 | 30 | $9.50 \times 10^5$ | 0 | 5.97 |

Table 3 below summarizes the results of tests against *Pseudomonas. aeruginosa*. All three trials were able to bring about a >6$log_{10}$ reduction in the viability titre of *P. aeruginosa* in a contact time of 5 minutes at room temperature indicating bactericidal activity against this organism.

TABLE 3

The activity of Composition I against *Pseudomonas aeruginosa*

| Trial | Contact Time (minutes) | CFU/Control Carrier | Average CFU Test Carrier | $Log_{10}$ Reduction |
|---|---|---|---|---|
| 1 | 5 | $2.04 \times 10^6$ | 0 | 6.31 |
| 2 | 5 | $2.04 \times 10^6$ | 0 | 6.31 |
| 3 | 5 | $2.04 \times 10^6$ | 0 | 6.31 |

Table 4 below summarizes the results of the suspension test. All three trials were able to bring about a >7 $log_{10}$ reduction in the viability titre of *P. aeruginosa* in a contact time of 30 seconds at room temperature.

TABLE 4

The activity of Composition I against *Pseudomonas aeruginosa*

| Trial | Contact Time (seconds) | CFU/Control Carrier | Average CFU Test Carrier | $Log_{10}$ Reduction |
|---|---|---|---|---|
| 1 | 30 | $2.30 \times 10^7$ | 0 | 7.36 |
| 2 | 30 | $2.30 \times 10^7$ | 0 | 7.36 |
| 3 | 30 | $2.30 \times 10^7$ | 0 | 7.36 |

Table 5 below summarizes the results of *S. choleraesuis* testing. All three trials were able to bring about a >6$log_{10}$ reduction in the viability titre of *Salmonella choleraesuis* in a contact time of 5 minutes at room temperature indicating bactericidal activity against this organism.

TABLE 5

The activity of Composition I against *Salmonella choleraesuis*

| Trial | Contact Time (minutes) | CFU/Control Carrier | Average CFU Test Carrier | $Log_{10}$ Reduction |
|---|---|---|---|---|
| 1 | 5 | $2.26 \times 10^6$ | 0 | 6.34 |
| 2 | 5 | $1.17 \times 10^6$ | 0 | 6.07 |
| 3 | 5 | $1.17 \times 10^6$ | 0 | 6.07 |

Table 6 below summarizes the results of the suspension test. All three trials were able to bring about a >6$log_{10}$ reduction in the viability titre of *Salmonella choleraesuis* in a contact time of 30 seconds at room temperature.

TABLE 6

The activity of Composition I against *Salmonella choleraesuis*

| Trial | Contact Time (seconds) | CFU/Control Carrier | Average CFU Test Carrier | $Log_{10}$ Reduction |
|---|---|---|---|---|
| 1 | 30 | $1.30 \times 10^6$ | 0 | 6.11 |
| 2 | 30 | $1.30 \times 10^6$ | 0 | 6.11 |
| 3 | 30 | $1.30 \times 10^6$ | 0 | 6.11 |

Table 7 below summarizes the results of the suspension test. All three trials were able to bring about a >6-$log_{10}$ reduction in the viability titre of Methicillin Resistant *S. aureus* a contact time of 30 seconds at room temperature indicating bactericidal activity against this organism.

TABLE 7

The activity of Composition I against Methicillin Resistant *S. aureus*

| Trial | Contact Time (seconds) | CFU/Control Carrier | Average CFU Test Carrier | $Log_{10}$ Reduction |
|---|---|---|---|---|
| 1 | 30 | $1.70 \times 10^6$ | 0 | 6.23 |
| 2 | 30 | $1.70 \times 10^6$ | 0 | 6.23 |
| 3 | 30 | $1.70 \times 10^6$ | 0 | 6.23 |

Table 8 below summarizes the results of the suspension test. All three trials were able to bring about a >6-$log_{10}$ reduction in the viability titre of Vancomycin Resistant *Enterucoccus* in a contact time of 30 seconds at room temperature indicating bactericidal activity against this organism.

TABLE 8

The activity of Composition I against Vancomycin Resistant *Enterococcus*

| Trial | Contact Time (seconds) | CFU/Control Carrier | Average CFU Test Carrier | $Log_{10}$ Reduction |
|---|---|---|---|---|
| 1 | 30 | $5.7 \times 10^6$ | 2 | 6.54 |
| 2 | 30 | $5.7 \times 10^6$ | 2 | 6.62 |
| 3 | 30 | $5.7 \times 10^6$ | 2 | 6.47 |

Table 9 below summarizes the results of the suspension test. All three trials were able to bring about a >6-$log_{10}$ reduction in the viability titre of *Acinetobacter baumannii* in time of 5 minutes at room temperature indicating bactericidal activity against this organism.

TABLE 9

The activity of Composition I against *Acinetobacter baumannii*

| Trial | Contact Time (minutes) | CFU/Control Carrier | Average CFU Test Carrier | $Log_{10}$ Reduction |
|---|---|---|---|---|
| 1 | 5 | $1.02 \times 10^6$ | 0 | 6.00 |
| 2 | 5 | $1.71 \times 10^6$ | 0 | 6.23 |
| 3 | 5 | $1.71 \times 10^6$ | 0 | 6.23 |

Table 10 below summarizes the results of the Carrier test. All three trials were able to bring about a >5-$log_{10}$ reduction in the viability titre of *Mycobacterium terrae* in a contact time of 5 minutes at room temperature indicating bactericidal activity against this organism.

TABLE 10

The activity of Composition I against *Mycobacterium terrae*

| Trials | Contact Time (minutes) | CFU/Control Carrier | Average CFU Test Carrier | $Log_{10}$ Reduction |
|---|---|---|---|---|
| 1 | 5 | $2.0 \times 10^5$ | 0 | 5.30 |
| 2 | 5 | $2.0 \times 10^5$ | 0 | 5.30 |
| 3 | 5 | $2.0 \times 10^5$ | 0 | 5.30 |

Table 11 below summarizes the results of the carrier test. All three trials were able to bring about a >5-$log_{10}$ reduction in the viability titre of *T. mentagrophytes* in a contact time of 5 minutes at room temperature indicating bactericidal activity against this organism.

TABLE 11

The activity of Composition I against *T. mentagrophytes*

| Trials | Contact Time (minutes) | CFU/Control Carrier | Average CFU Test Carrier | $Log_{10}$ Reduction |
|---|---|---|---|---|
| 1 | 5 | $1.13 \times 10^5$ | 0 | 5.05 |
| 2 | 5 | $1.13 \times 10^5$ | 0 | 5.05 |
| 3 | 5 | $1.13 \times 10^5$ | 0 | 5.05 |

As seen in Table 12 below, Composition I was able to bring about a >4 $log_{10}$ in the viability titre of the Poliovirus in a contact time of 5 minutes at 20±1° C., indicating virucidal activity against this organism.

TABLE 12

The activity of Composition I against *Poliovirus* type 1 (Sabin)

| Trials | Contact Time (minutes) | PFU/Control Carrier | Average PFU Test Carrier | $Log_{10}$ Reduction |
|---|---|---|---|---|
| 1 | 5 | $1.28 \times 10^4$ | 0 | 4.10 |
| 2 | 5 | $1.28 \times 10^4$ | 0 | 4.10 |
| 3 | 5 | $8.00 \times 10^4$ | 0 | 4.70 |

EXAMPLE II

This example further illustrates the mycobactericidal activity of Composition I, as well as the synergy of the 2-furan carboxylic acid and hydrogen peroxide in the mixture. The methodology employed for the evaluation of mycobactericidal efficacy is the quantitative carrier method described above (ASTM Standard E2111). Currently, the passing standard in Canada for noncritical disinfection is a greater than 4-$log_{10}$ reduction in viable numbers of microorganisms, while for semicritical and critical applications it is greater than 6-$log_{10}$.

The results for Composition I and alternative compositions A, B, and C are tabled below.

TABLE II

| TEST SAMPLE | $Log_{10}$ reduction |
|---|---|
| Composition I | 5.30 in 5 min. |
| (A) 0.50% 2-furoic acid in DI water at a pH of 1.8 | <2.0 in 5 min. |
| (B) 0.50% Hydrogen peroxide in DI water at a pH of 1.8 | <1.0 in 5 min. |
| (C) Composition I without 2-furoic acid | <1.0 in 5 min. |

DI water = deionized water
2-furoic acid = 2-furan carboxylic acid

It is seen from the above results that there is a clear, unexpected synergy between the 2-furoic acid and one or more of the other components of Composition I, as a simple additive effect would yield a $log_{10}$ reduction of less than 4.0 $log_{10}$.

EXAMPLE III

In this example, the sporicidal and mycobactericidal properties of Composition II are illustrated. Once again, the quantitative carrier method was used. However, the experiments were run at a temperature of 54° C. to simulate use of the disinfectant in an endoscope processing machine. The surrogate organism for measuring sporicidal efficacy was *Bacillus subtilis*. The surrogate organism for measuring mycobactericidal efficacy was *mycobacterium terrae*. Once more, relevant comparative examples (Compositions A, B, and C) are included which describe the synergy between the 2-furoic acid and other components of the solution. The contact time was 15 minutes.

TABLE III

| TEST SAMPLE | $Log_{10}$ reduction (*bacillus subtilis*) | $Log_{10}$ reduction (*mycobacterium terrae*) |
|---|---|---|
| Composition II | 6.04 | 7.00 |
| (A) Composition II with 0.50% active H2O2 and no 2-furoic acid | 4.60 | |
| (B) Composition II with no 2-furoic acid | 4.90 | |
| (C) Composition II with 0.75% 2-furoic acid and no H2O2 | <<4.0 | |

2-furoic acid = 2-furan carboxylic acid

It is seen from the above results that the addition of a small amount of 2-furoic acid to a 0.75% active hydrogen peroxide solution (Composition II) will increase the efficacy of the solution by more than 1 order of magnitude in relation to 0.75% hydrogen peroxide alone (Composition B), and by more than 2 orders of magnitude with respect to a 2-furoic acid based solution (Composition C).

EXAMPLE IV

Composition I was evaluated for its acute skin and eye, as well as oral toxicity. The standard methods for testing chemicals established by the OECD (standards OECD Sec. 404, 405, 420, respectively) were used and the results are summarized below.

| TEST SAMPLE | Acute eye irritation class | Acute skin irritation | Oral $LD_{50}$ |
|---|---|---|---|
| Composition I | Minimally irritating | Irritation index 0.50 | >2000 mg/Kg |

In parallel testing of skin irritation with a commercial surgical soap based on chloroxylenol, it was found that the hand soap, in spite of containing a variety of ingredients to minimize skin irritation and promote moisturizing, scored a much higher irritation index of 2.25. An acute skin irritation index score between 0.01 and 1.99 classifies a substance as a slight irritant, while a score of 2.00-5.00 means that the substance is a moderate irritant. Furthermore, an oral $LD_{50}$ score of over 2000 mg/Kg means that the substance is classified as nontoxic when ingested.

EXAMPLE V

Composition I was subjected to an accelerated hot stability test in order to evaluate hydrogen peroxide stability in the solution. A sample was subjected to a temperature of 50° C. for 1 week and the hydrogen peroxide content was measured by iodometric titration before and after the test. The observed loss of hydrogen peroxide was 3.41% of the initial concentration which indicates that, in practice, the solution would have a room temperature shelf life in excess of 1 year.

The following components are used in the examples which follow:

Phosphorous-based Compounds and/or Cation Sequestering Agents $H_3PO_4$=phosphoric acid BRIQUEST ADPA-60AW (HEDP)=1-hydroxyethylidene-1,1,-diphosphonic acid (sold by Allbright and Wilson)

BRIQUEST ADPA-60SH =sodiums salt of 1-hydroxyethylidene-1,1,-diphosphonic acid (sold by Allbright and Wilson)

Anionic Surfactants/hydrotropes

Biosoft S-100 (DDBSA)=dodecyl benzene sulfonic acid (manufactured by Stepan)

Dowfax C10L=C10 alkylated sulfonated diphenyl oxide disodium salt (manufactured by the Dow Chemical Company)

C6 DOWFAX hydrotrope=C6 alkylated sulfonated diphenyl oxide disodium salt (manufactured by the Dow Chemical Company)

sodium xylene sulfonate

Non-ionic Surfactants (Emulsifiers)

Alfonic L610-3.5=C6-C10 alkyl, 3.5 moles of ethylene oxide (EO) alcohol ethoxylate (AE) (manufactured by Condea Vista)

Corrosion Inhibitors

Cobratec 35 G=1,2,3 benzotriazole (manufactured by PMC Specialties Group)

sodium molybdate

Buffers citric acid

NaOH=sodium hydroxide

KOH=potassium hydroxide $CaCO_3$=calcium carbonate

EXAMPLE VI

Solutions A, B, C, D and E were prepared in accordance with Table VIa below and their activities against various organisms are contained in Tables VIb, VIc and VId below.

TABLE VIa

| Ingredient | A % w/w | B % w/w | C % w/w | D % w/w | E % w/w |
|---|---|---|---|---|---|
| Deionized Water | Up to 100 | Up to 100 | Up to 100 | Up to 100 | Up to 100 |
| Phosphoric acid (75%) | 0.15 | 0.15 | 0.15 | 0.15 | 0.15 |
|  | 0.11 | 0.11 | 0.11 | 0.11 | 0.11 |
| Briquest ADPA-60AW (60%) | 0.48 | 0.48 | 0.48 | 0.48 | 0.48 |
|  | 0.29 | 0.29 | 0.29 | 0.29 | 0.29 |
| C6 Dowfax Hydrotrope (40%) | 0.18 | 0.18 | 0.18 | 0.18 | 0.18 |
|  | 0.07 | 0.07 | 0.07 | 0.07 | 0.07 |
| Biosoft S-100 (98%) | 0.18 | 0.18 | 0.18 | 0.18 | 0.18 |
|  | 0.18 | 0.18 | 0.18 | 0.18 | 0.18 |
| Alfonic L610-3.5 (100%) | 0.05 | 0.05 | 0.05 | 0.05 | 0.05 |
|  | 0.05 | 0.05 | 0.05 | 0.05 | 0.05 |
| Hydrogen Peroxide (50%) | 1.10 | 1.10 | 1.10 | 1.10 | 1.10 |
|  | 0.55 | 0.55 | 0.55 | 0.55 | 0.55 |
| Benzyl alcohol (99%) | 2.50 | 2.50 | 2.50 | 2.50 | 0 |
|  | 2.50 | 2.50 | 2.50 | 2.50 | 0 |
| pH (adjust with effective amount of NaOH) | 1.8 | 2.4 | 3.0 | 4.0 | 1.8 |

The active concentration in solution is shown in bold.

TABLE VIb

The activity of Solutions A-E against *M. terrae* (QCT I)

| Solution | Contact Temp | Contact Time | CFU/control Carrier | CFU/test Carrier | $Log_{10}$ Red'n |
|---|---|---|---|---|---|
| A | RT | 5 min | $1.83 \times 10^6$ | 0 | 6.26 |
| B | RT | 5 min | $1.83 \times 10^6$ | 0 | 6.26 |
| C | RT | 5 min | $1.83 \times 10^6$ | 0 | 6.26 |
| D | RT | 5 min | $1.83 \times 10^6$ | 2 | 6.03 |
| E | RT | 5 min | $1.83 \times 10^6$ | TNTC | * |

TNTC: too numerous to count (means there is no activity)
RT = room temperature

TABLE VIc

The activity of Solutions A-E against *T mentagrophytes* (QCT I)

| Solution | Contact Temp | Contact Time | CFU/control Carrier | CFU/test Carrier | $Log_{10}$ Red'n |
|---|---|---|---|---|---|
| A | RT | 5 min | $2.53 \times 10^5$ | 0 | 5.4 |
| B | RT | 5 min | $2.17 \times 10^5$ | 0 | 5.3 |
| C | RT | 5 min | $2.17 \times 10^5$ | 2 | 5.21 |
| D | RT | 5 min | $2.17 \times 10^5$ | 5 | 4.7 |
| E | RT | 5 min | $2.17 \times 10^5$ | TNTC | * |

RT = room temperature

TABLE VId

The activity of Solutions A-E against *Staphylococcus aureus* (QCT I)

| Solution | Contact Temp | Contact Time | CFU/control Carrier | CFU/test Carrier | $Log_{10}$ Red'n |
|---|---|---|---|---|---|
| A | RT | 5 minutes | $6.67 \times 10^6$ | 0 | 6.82 |
| B | RT | 5 minutes | $6.67 \times 10^6$ | 0 | 6.82 |
| C | RT | 5 minutes | $6.67 \times 10^6$ | 0 | 6.82 |
| D | RT | 5 minutes | $6.67 \times 10^6$ | 0 | 6.82 |
| E | RT | 5 minutes | $1.66 \times 10^6$ | 0 | 6.22 |

RT = room temperature

Skin and eye irritation results for Solution B:

|  | Acute skin irritation | Acute eye irritation class |
|---|---|---|
| Solution B | Irritation index 0.0 | Non irritating |

EXAMPLE VII

Solution F was prepared in accordance with Table VIIa below and its activity against *T. mentagrophytes* is contained in Table VIIb below.

TABLE VIIa

| Ingredient | F % w/w |
|---|---|
| Deionized Water | Up to 100 |
| Phosphoric acid (75%) | 0.15 |
|  | 0.11 |
| Briquest ADPA-60AW (60%) | 0.48 |
|  | 0.29 |
| C6 Dowfax Hydrotrope (40%) | 0.18 |
|  | 0.07 |
| Biosoft S-100 (98%) | 0.18 |
|  | 0.18 |
| Alfonic L610-3.5 (100%) | 0.05 |
|  | 0.05 |
| Hydrogen Peroxide (50%) | 1.10 |
|  | 0.55 |
| Benzyl alcohol (99%) | 1.50 |
|  | 1.50 |
| pH (adjust with effective amount of NaOH) | 1.8 |

The active concentration in solution is shown in bold.

TABLE VIIb

The activity of Solution F against *T. mentagrophytes* (QCT I)

| Solution | Contact Temp | Contact Time | CFU/control Carrier | CFU/test Carrier | $Log_{10}$ Red'n |
|---|---|---|---|---|---|
| F | RT | 5 min | $3.8 \times 10^5$ | 0 | 5.58 |

RT = room temperature

EXAMPLE VIII

Solutions G, H and I were prepared in accordance with Table VIIIa below and their activities against various organisms are contained in Tables VIIIb, VIIIc, VIIId and VIIIe below.

TABLE VIIIa

| Ingredient | G % w/w | H % w/w | I % w/w |
|---|---|---|---|
| Deionized water | To 100 | To 100 | To 100 |
| Briquest ADPA 60AW (60%) | 0.50 | 0.50 | 0.50 |
|  | 0.30 | 0.30 | 0.30 |
| Dowfax C10L (45%) | 0.19 | 0.19 | 0.19 |
|  | 0.09 | 0.09 | 0.09 |
| Biosoft S-100 (98%) | 0.18 | 0.18 | 0.18 |
|  | 0.18 | 0.18 | 0.18 |
| Alfonic L610-3.5 (100%) | 0.05 | 0.05 | 0.05 |
|  | 0.05 | 0.05 | 0.05 |
| Citric acid (99%) | 0.50 | 0.50 | 0.50 |
|  | 0.50 | 0.50 | 0.50 |
| Phosphoric acid (75%) | 2.00 | 2.00 | 2.00 |
|  | 1.50 | 1.50 | 1.50 |
| Hydrogen Peroxide (50%) | 4.00 | 3.60 | 4.00 |
|  | 2.00 | 2.00 | 2.00 |
| Sodium Molybdate (99%) | 0.01 | 0.01 | 0.01 |
|  | 0.01 | 0.01 | 0.01 |
| Cobratec 35 G (35% benzotriazole) | 0.50 | 0.50 | 0.50 |
|  | 0.18 | 0.18 | 0.18 |
| Benzyl alcohol (99%) | 2.40 | 2.00 | 2.00 |
|  | 2.38 | 1.98 | 1.98 |
| NaOH (up to pH = 4) | Up to pH = 4.0 | Up to pH = 4.0 | Up to pH = 5.0 |

The active concentration in solution is shown in bold.

TABLE VIIIb

The activity of Solutions G, H and I against *M. terrae* (QCT I)

| Solution | Contact Temp | Contact Time | CFU/control Carrier | CFU/test Carrier | $Log_{10}$ Red'n |
|---|---|---|---|---|---|
| G | RT | 15 min | $8.3 \times 10^6$ | 0 | 6.92 |
| H | RT | 15 min | $8.3 \times 10^6$ | 0 | 6.92 |
| I | RT | 15 min | $8.3 \times 10^6$ | 0 | 6.92 |

RT = room temperature

TABLE VIIIc

The activity of Solutions G, H and I against *T. mentagrophytes* (QCT I)

| Solution | Contact Temp | Contact Time | CFU/control Carrier | CFU/test Carrier | $Log_{10}$ Red'n |
|---|---|---|---|---|---|
| G | RT | 15 min | $2.7 \times 10^5$ | 0 | 5.43 |
| H | RT | 15 min | $2.7 \times 10^5$ | 0 | 5.43 |
| I | RT | 15 min | $2.7 \times 10^5$ | 0 | 5.43 |

RT = room temperature

TABLE VIIId

The activity of Solutions G, H and I against *Polio virus* (ASTM E1053(97)

| Solution | Contact Temp | Contact Time | CFU/control Carrier | CFU/test Carrier | $Log_{10}$ Red'n |
|---|---|---|---|---|---|
| G | RT | 15 min | $6.87 \times 10^4$ | 0 | 4.84 |
| H | RT | 15 min | $6.87 \times 10^4$ | 0 | 4.84 |
| I | RT | 15 min | $6.87 \times 10^4$ | 0 | 4.84 |

RT = room temperature

TABLE VIIIe

The activity of Solutions G and H against *B. subtilis* (QCT I)

| Solution | Contact Temp | Contact Time | CFU/control Carrier | CFU/test Carrier | $Log_{10}$ Red'n |
|---|---|---|---|---|---|
| G | RT | 6 hrs | $8.43 \times 10^6$ | 0 | 6.92 |
| H | RT | 6 hrs | $8.43 \times 10^6$ | 0 | 6.92 |

RT = room temperature

EXAMPLE IX

Solutions J, K, L and M were prepared in accordance with Table IXa below and their activities against *M. terrae* are given in Table IXb below.

TABLE IXa

| Ingredient | J % w/w | K To 100 | L % w/w | M % w/w |
|---|---|---|---|---|
| Deionized water | To 100 | 1.0 | To 100 | To 100 |
| Briquest ADPA 60AW (60%) | 1.0 | 1.0 | 1.0 | 1.0 |
|  | 0.60 | 0.60 | 0.60 | 0.60 |
| Dowfax C10L (45%) | 0.19 | 0.09 | 0.19 | 0.19 |
|  | 0.09 | 0.09 | 0.09 | 0.09 |
| Biosoft S-100 (98%) | 0.18 | 0.18 | 0.18 | 0.18 |
|  | 0.18 | 0.18 | 0.18 | 0.18 |
| Alfonic L610-3.5 (100%) | 0.05 | 0.05 | 0.05 | 0.05 |
|  | 0.05 | 0.05 | 0.05 | 0.05 |
| Phosphoric acid (75%) | 2.00 | 2.00 | 2.00 | 2.00 |
|  | 1.50 | 1.50 | 1.50 | 1.50 |
| Hydrogen Peroxide (50%) | 4.00 | 4.00 | 4.00 | 4.00 |
|  | 2.00 | 2.00 | 2.00 | 2.00 |
| Sodium Molybdate (99%) | 0.01 | 0.01 | 0.01 | 0.01 |
|  | 0.01 | 0.01 | 0.01 | 0.01 |
| Cobratec 35 G (35% benzotriazole) | 0.50 | 0.50 | 0.50 | 0.50 |
|  | 0.18 | 0.18 | 0.18 | 0.18 |
| 2-Furoic acid (99%) | 1.0 | 0.5 | 2.7 | 2.7 |
|  | 0.99 | 0.50 | 2.67 | 2.67 |
| Benzyl alcohol (99%) | 0 | 0 | 0 | 2.0 |
|  | 0 | 0 | 0 | 1.98 |
| NaOH (up to pH = 4) | Up to pH = 3.0 | Up to pH = 3.0 | Up to pH = 4.0 | Up to pH = 4.0 |

The active concentration in solution is shown in bold.
2-Furoic acid = 2 furan carboxylic acid TABLE IXb The activity of Solutions J, K, L, and M against *M. terrae* (QCT I)

| Solution | Contact Temp | Contact Time | CFU/control Carrier | CFU/test Carrier | $Log_{10}$ Red'n |
|---|---|---|---|---|---|
| J | RT | 15 min | $1.06 \times 10^7$ | 0 | 7.02 |
| K | RT | 15 min | $1.06 \times 10^7$ | 46 | 5.4 |
| L | RT | 15 min | $1.24 \times 10^7$ | 1 | 7.09 |
| M | RT | 15 min | $9.33 \times 10^6$ | 0 | 6.77 |

RT = room temperature

EXAMPLE X

Solutions P and Q were prepared in accordance with Table Xa and Xb below and their activity against *B. subtilis* is shown in Table Xc.

TABLE Xa

| Ingredient | N % w/w | O % w/w |
|---|---|---|
| Deionized water | To 100 | To 100 |
| Briquest ADPA 60AW (60%) | 3.0 | 3.0 |
|  | 1.80 | 1.80 |
| Sodium xylene sulfonate (40%) | 10 | 10 |
|  | 4.00 | 4.00 |
| Propylene glycol (99%) | 10 | 10 |
|  | 9.90 | 9.90 |
| Sodium Molybdate (99%) | 0.5 | 0.5 |
|  | 0.50 | 0.50 |
| Cobratec 35 G (35% benzotriazole) | 15.0 | 15.0 |
|  | 5.25 | 5.25 |
| 2-Furoic acid (99%) | 10.0 | 10.0 |
|  | 9.90 | 9.90 |
| Citric acid (99%) | 1.0 | 1.0 |
|  | 1.00 | 1.00 |
| Benzyl alcohol (99%) | 10 | 10 |
|  | 9.90 | 9.90 |
| NaOH (up to pH = 4) | Up to pH = 4.0 | Up to pH = 4.0 |

The active concentration in solution is shown in bold.

TABLE Xb

| Ingredient | P % w/w | Q % w/w |
|---|---|---|
| Formulation N | 4 | 0 |
| Formulation O | 0 | 4 |
| Hydrogen peroxide (50%) | 3 | 3 |
| Water (200 ppm hardness) | To 100 | To 100 |

TABLE Xc

The activity of Solutions P and Q against *B. subtilis* (QCT I)

| Solution | Contact Temp | Contact Time | CFU/control Carrier | CFU/test Carrier | $Log_{10}$ Red'n |
|---|---|---|---|---|---|
| P | 54° C. | 15 min | $1.08 \times 10^7$ | 20 | 6.13 |
| Q | 54° C. | 15 min | $1.08 \times 10^7$ | 1 | 6.91 |

EXAMPLE XI

Solutions R and S were prepared in accordance with Table XIa below and their activity against a selected organism is shown in Table XIb and XIc below.

TABLE XI

| Ingredient | R % w/w | S % w/w |
|---|---|---|
| Water ppm hardness | To 100 | To 100 |
| Briquest ADPA 60AW (60%) | 0.12 | 0.12 |
|  | 0.07 | 0.07 |
| Sodium Molybdate (99%) | 0.02 | 0.02 |
|  | 0.02 | 0.02 |
| Cobratec 99 (99% benzotriazole) | 0.3 | 0.3 |
|  | 0.30 | 0.30 |
| 2-Furoic acid (99%) | 0.4 | 0.05 |
|  | 0.40 | 0.40 |
| H2O2 (50%) | 0.75 | 0.25 |
|  | 0.40 | 0.12 |
| CaCO3 or KOH | Up to pH = 6.0 | Up to pH = 4.0 |

The active concentration in solution is shown in bold.

TABLE XIb

The activity of Solution R against *B. subtilis* (QCT I)

| Solution | Contact Temp | Contact Time | CFU/control Carrier | CFU/test Carrier | $Log_{10}$ Red'n |
|---|---|---|---|---|---|
| R | 54° C. | 15 min | $1.3 \times 10^6$ | 0 | 6.11 |

TABLE XIc

The activity of Solution S against *M. terrae* (QCT I)

| Solution | Contact Temp | Contact Time | CFU/control Carrier | CFU/test Carrier | $Log_{10}$ Red'n |
|---|---|---|---|---|---|
| S | 54° C. | 10 min | $4.26 \times 10^6$ | 0 | 6.62 |

EXAMPLE XII

Solution T was prepared in accordance with Table XIIa below and the activity against *M. terrae* is summarized in Table XIIb below.

TABLE XIIa

| Ingredient | T % w/w |
|---|---|
| Deionized Water | Up to 100 |
| Phosphoric acid (75%) | 0.15 |
| | 0.11 |
| Briquest ADPA-60AW (60%) | 0.48 |
| | 0.29 |
| C6 Dowfax Hydrotrope (40%) | 0.18 |
| | 0.07 |
| Biosoft S-100 (98%) | 0.18 |
| | 0.18 |
| Alfonic L610-3.5 (100%) | 0.05 |
| | 0.05 |
| Hydrogen Peroxide (50%) | 1.10 |
| | 0.55 |
| Benzyl alcohol (99%) | 3.0 |
| | 3.00 |
| pH adjusted using effective amount of NaOH buffer | 2.4 |

The active concentration in solution is shown in bold.

TABLE XIIb

The activity of Solution T against *M. terrae* (QCT I)

| Solution | Contact Temp | Contact Time | CFU/control Carrier | CFU/test Carrier | $Log_{10}$ Red'n |
|---|---|---|---|---|---|
| T | RT | 1 min | $8.4 \times 10^6$ | 3 | 6.56 |

RT = room temperature

In the above examples, Solutions A, B, C, D, E, F, and T are hard surface disinfectants. Solutions G, H, I, J, K, L, M are high level disinfectants and sterilants and can also be used as hard surface cleaners. Solutions N, O, P, Q, R, and S are high level disinfectants and chemosterilants and can also be used for medical and other devices.

The foregoing examples are for illustrative purposes only and shall not be construed so as to restrict the scope of the invention as defined by the following claims.

We claim:

1. An aqueous solution effective in killing mycobacteria and spores, having a pH of from 0.6 to 7 and comprising:
   (a) hydrogen peroxide in a concentration of from 0.01 to 6% w/w, based on the total weight of the solution; and
   (b) 2-furan carboxylic acid in a concentration of from 0.01 to 8% w/w, based on the total weight of the solution.

2. A solution according to claim 1 wherein said 2-furan carboxylic acid is present in a concentration of from 0.1 to 4% w/w, based on the total weight of the solution.

3. A solution according to claim 2 wherein said 2-furan carboxylic acid is present in a concentration of from 0.1 to 2.5% w/w, based on the total weight of the solution.

4. A solution according to claim 1 further comprising benzyl alcohol.

5. A solution according to claim 4 further comprising benzoic acid.

6. A solution according to claim 4 further comprising salicylic acid.

7. A solution according to claim 1 further comprising at least one nonionic surfactant in a concentration of from 0.005 to 3% w/w, based on the total weight of the solution.

8. A solution according to claim 7 wherein said at least one nonionic surfactant is present in a concentration of from 0.01 to 3% w/w, based on the total weight of the solution.

9. A solution according to claim 8 wherein said at least one nonionic surfactant is present in a concentration of from 0.01 to 1% w/w, based on the total weight of the solution.

10. A solution according to claim 7 wherein said at least one nonionic surfactant is chosen from (a) ethoxylated alcohols and alkylglycosides having a hydrophile lyophile balance from 5 to 15; and (b) a sufficiently water-soluble block copolymer of ethylene oxide or propylene oxide.

11. A solution according to claim 10 wherein said at least one nonionic surfactant is a sufficiently water-soluble block copolymer of ethylene oxide or propylene oxide, a C6-C10 alkyl, 3.5 moles of ethylene oxide (EO) alcohol ethoxylate, or a combination thereof.

12. A solution according to claim 1 further comprising at least one cation sequestering agent in a concentration of from 0.01 to 6% w/w, based on the total weight of the solution.

13. A solution according to claim 12 wherein said cationic sequestering agent is present in a concentration of from 0.05 to 2% w/w, based on the total weight of the solution.

14. A solution according to claim 12 wherein said cation sequestering agent is 1-hydroxyethylidene-1,1-diphosphonic acid.

15. A solution according to claim 1 further comprising at least one anionic surfactant chosen from (a) C8-C16 alkyl benzene sulfonic acids and alkali metal, alkaline earth metal, ammonium or alkylamine salts thereof (b) C8-C18 alkyl sulfonic acids; (c) C8-C16 alkyl sulfates; and (d) C6-C12 alkyl diphenyl oxide sulfonate in a concentration of from 0.01 to 10% w/w, based on the total weight of the solution.

16. A solution according to claim 15 wherein said at least one anionic surfactant is present in a concentration of from 0.01 to 6% w/w, based on the total weight of the solution.

17. A solution according to claim 16 wherein said at least one anionic surfactant is present in a concentration of from 0.05 to 3% w/w, based on the total weight of the solution.

18. A solution according to claim 15 wherein said at least one anionic surfactant is chosen from alkyl benzene sulfonic acids and C6-C10 alkyl diphenyl oxide sulfonates.

19. A solution according to claim 15 wherein said at least one anionic surfactant is chosen from a C6 alkylated sulfonated diphenyl oxide sodium salt, a C10 alkylated sulfonated diphenyl oxide sodium salt, and dodecyl benzene sulfonic acid.

20. A solution according to claim 1 having a pH of from 0.6 to 5.

21. A solution according to claim 20 having a pH of from 2 to 4.

22. A solution according to claim 1 further comprising at least one buffer in an amount effective to buffer the solution to said pH.

23. A solution according to claim 22 wherein said at least one buffer is chosen from phosphoric acid, citric acid, glycolic acid, sodium carbonate, calcium carbonate, potassium hydroxide, sodium hydroxide, ethanolamine and lactic acid.

24. A solution according to claim 1 further comprising at least one corrosion inhibitor in a concentration of from 0.001 to 15% w/w, based on the total weight of the solution.

25. A solution according to claim 24 wherein the at least one corrosion inhibitor is present in a concentration of from 0.01 to 5% w/w, based on the total weight of the solution.

26. A solution according to claim 25 wherein the at least one corrosion inhibitor is present in a concentration of from 0.01 to 1% w/w, based on the total weight of the solution.

27. A solution according to claim 24 wherein the at least one corrosion inhibitor is chosen from 1,2,3 benzotriazole, sodium molybdate, sodium nitrite, sodium bisulfate, sodium metabisulfate, chromates, borates, phosphates, polyphosphates, sodium benzoate, sodium gluconate and sodium silicate.

28. A solution according to claim 1 wherein said hydrogen peroxide is present in a concentration of from 0.25 to 4% w/w, based on the total weight of the solution.

29. A solution according to claim 1 further comprising a hydrotrope in a concentration of from 0.01 to 15% w/w, based on the total weight of the solution.

30. A solution according to claim 29 wherein said hydrotrope is sodium xylene sulfonate.

31. A solution according to claim 1 further comprising a solvent in a concentration of from 0.01 to 15% w/w, based on the total weight of the solution.

32. A solution according to claim 31 wherein said solvent is a glycol or glycol ether.

33. A solution according to claim 1 further comprising benzoic acid.

34. A solution according to claim 1 further comprising salicylic acid.

35. A concentrated, aqueous, acidic disinfecting solution which may be diluted with water to provide a solution according to claim 1.

36. A solution according to claim 35 wherein the 2-furan carboxylic acid is present in a concentration up to 30% w/w, based on the total weight of the solution.

37. A multi-component system which can be combined to provide a disinfecting solution according to claim 1.

38. A method of disinfecting equipment in place comprising the steps of
    (a) providing a solution according to claim 1; and
    (b) circulating said solution in place through said equipment at a temperature of from 20 to 60 degrees Celsius to disinfect the equipment.

39. A method of disinfecting a surface comprising the step of applying a solution according to claim 1 to the surface to disinfect the surface.

* * * * *

UNITED STATES PATENT AND TRADEMARK OFFICE
CERTIFICATE OF CORRECTION

| | |
|---|---|
| PATENT NO. | : 7,354,604 B2 |
| APPLICATION NO. | : 10/712990 |
| DATED | : April 8, 2008 |
| INVENTOR(S) | : Ramirez et al. |

It is certified that error appears in the above-identified patent and that said Letters Patent is hereby corrected as shown below:

Title Page; item(s) (56); OTHER PUBLICATIONS should include:

Database WPI, Section Ch, Week 199615, Derwent Publications Ltd., London, GB, Class D22, AN 1996-149587 XP002287351 & RU 2040275C1 (BIOL INSTR MFR RES INST) 27JUL1995 abstract Database Chemabs 'Online!, Chemical Abstract Service, Columbus, OH, US, XP002287350 retrieved from STN-INTERNATIONAL Database accession no. 136:351642 abstract Database WPI, Section Ch, Week 199918, Derwent Publications Ltd., London, GB, Class C03, AN 1999-205420 XP002287352 & CN 1 201 594 A (Wang L), 16DEC1998 abstract S. Block, DISINFECTION, STERILIZATION, AND PRESERVATION, Fourth Edition 1991, pgs. 167-172, 178-180, 256-261, 263-271, 1010-1013, 1029

COLUMN 2, LINE 39
"lglycosides having a hydrophile lyophile balance from 5 to"
should read:
"lglycosides having a hydrophile lypophile balance from 5 to"

COLUMN 5, LINE 38
"ethoxylated alcohols and alkylglycosides of hydrophile lyo-"
should read:
"ethoxylated alcohols and alkylglycosides of hydrophile lypo-"

COLUMN 6, LINE 4
"include ethylenediaminetettraacetic acid, hydroxyethyl-eth-"
should read:
"include ethylenediaminetetraacetic acid, hydroxyethyl-eth-"

COLUMN 6, LINE 17
"agents may be added to modify its Theological properties,"
should read:
"agents may be added to modify its rheological properties,"

UNITED STATES PATENT AND TRADEMARK OFFICE
CERTIFICATE OF CORRECTION

PATENT NO. : 7,354,604 B2
APPLICATION NO. : 10/712990
DATED : April 8, 2008
INVENTOR(S) : Ramirez et al.

It is certified that error appears in the above-identified patent and that said Letters Patent is hereby corrected as shown below:

COLUMN 18, LINE 37 (TABLE VIb)

| D | RT | 5 min | 1.83 X 106 | 2 | 6.03 | should read:

| D | RT | 5 min | $1.83 \times 10^6$ | 2 | 6.03 |

COLUMN 18, LINE 38 (TABLE VIb)

| E | RT | 5 min | 1.83 X 106 | TNTC | * | should read:

| E | RT | 5 min | $1.83 \times 10^6$ | TNTC | * |

COLUMN 24, LINE 33
"alcohols and alkylglycosides having a hydrophile lyophile"
should read:
"alcohols and alkylglycosides having a hydrophile lypophile"

Signed and Sealed this

Twenty-sixth Day of May, 2009

JOHN DOLL
*Acting Director of the United States Patent and Trademark Office*